US009470584B2

(12) United States Patent
Pompei et al.

(10) Patent No.: US 9,470,584 B2
(45) Date of Patent: Oct. 18, 2016

(54) METHOD AND APPARATUS FOR ACCURATE DETECTION OF FEVER

(71) Applicant: Exergen Corporation, Watertown, MA (US)

(72) Inventors: Francesco Pompei, Boston, MA (US); Janette H. Lee, Everett, MA (US); Jason N. Jarboe, Somerville, MA (US)

(73) Assignee: Exergen Corporation, Watertown, MA (US)

( * ) Notice: Subject to any disclaimer, the term of this patent is extended or adjusted under 35 U.S.C. 154(b) by 748 days.

(21) Appl. No.: 13/685,095

(22) Filed: Nov. 26, 2012

(65) Prior Publication Data

US 2014/0149065 A1 May 29, 2014

Related U.S. Application Data

(63) Continuation of application No. PCT/US2011/038453, filed on May 27, 2011.

(60) Provisional application No. 61/349,026, filed on May 27, 2010.

(51) Int. Cl.
*G06F 19/00* (2011.01)
*G01K 13/00* (2006.01)
*A61B 5/01* (2006.01)

(52) U.S. Cl.
CPC ............... *G01K 13/002* (2013.01); *A61B 5/01* (2013.01)

(58) Field of Classification Search
CPC ............ A61K 2300/00; A61B 5/6824; A61B 5/7267
USPC .................. 702/131, 182–185, 188
See application file for complete search history.

(56) References Cited

U.S. PATENT DOCUMENTS

| | | | |
|---|---|---|---|
| 2007/0161921 A1 | 7/2007 | Rausch | |
| 2008/0262782 A1 | 10/2008 | Pompei | |
| 2011/0093249 A1* | 4/2011 | Holmes et al. | 703/6 |

OTHER PUBLICATIONS

Mackowiak, P.A., and Wasserman S.S., "Physicians' Perceptions Regarding Body Temperature in Health and Disease", Southern Medical Journal, 88(9): 934-938 (1995).
Notification Concerning Transmittal of International Preliminary Report on Patentability for PCT/US2011/038453, date of mailing Dec. 6, 2012.

* cited by examiner

*Primary Examiner* — Edward Raymond
(74) *Attorney, Agent, or Firm* — Hamilton, Brook, Smith & Reynolds, P.C.

(57) ABSTRACT

The present invention relates to more accurate indication of fever. Temperature data from a large population of individuals are obtained and the temperature data are processed to determine a threshold, at a fever bump, above a normal range of distribution. The fever threshold, along with an individual's temperature, is used to indicate if the individual has a fever. Further, circadian information may be utilized to adjust the temperature data for an individual or the population of individuals.

48 Claims, 4 Drawing Sheets

METHOD AND APPARATUS FOR ACCURATE DETECTION OF FEVER

RELATED APPLICATIONS

This application is a continuation of International Application No. PCT/US2011/038453, which designated the United States and was filed on May 27, 2011, published in English, which claims the benefit of U.S. Provisional Application No. 61/349,026, filed on May 27, 2010, the entire teachings of which are incorporated herein by reference.

BACKGROUND

Fever is a commonly used medical indicator characterized by elevation of body temperature above a normal range. The normal range for human body temperature may vary, from person to person, based on external temperatures, age, sex, and level of activity of the person, and time of the day. For example, most individuals tend to have lower temperature readings in the second half of the sleep cycle. Further, body temperature measurements tend to change when a person is cold, sleepy, or hungry.

The average oral temperature is an adult is about 36.8° C. (98.2° F.). However, individuals are not expected to have the same exact temperature at all times during the course of a day. Temperature cycles regularly vary throughout the day and are believed to be controlled by a person's circadian rhythm/cycle.

Body temperatures are not always constant and may vary during the day based on the circadian cycle. As such, normal body temperature may vary as much as 1° F. (0.5° C.) for individuals throughout a day, which can lead to errors in assessing elevation of body temperature as true fevers indicating physiological disease processes.

For individuals, throughout the day, because body temperature varies with circadian cycle, it is known that two different temperature thresholds can be used to determine fever depending on time of the day.

SUMMARY

Certain embodiments of the present invention relate to a temperature detector that includes a temperature sensor and a processor. The temperature sensor obtains a temperature measurement and the processor adjusts the temperature measurement to establish more accurate detection of fever and improve sensitivity and specificity of fever detection.

Further embodiments of the present invention relate to a temperature detection method that includes obtaining a temperature measurement and adjusting the temperature measurement according to a circadian filter in order to establish more accurate detection of fever against a fever threshold.

Some embodiments of the present invention relate to method for processing temperature data that includes obtaining temperature data from large population and, from the temperature data, determining a fever threshold, at a fever bump, above a normal temperature distribution.

Certain other embodiments of the present invention relate to a temperature detector that includes a temperature sensor and a processor. The temperature sensor obtains temperature data from a large population and the processor processes the temperature data to determine a fever threshold, at a fever bump, above a normal temperature distribution.

Certain embodiments relate to a temperature detector that includes a temperature sensor, a processor, and an indicator. The temperature sensor obtains temperature data from a plurality of individuals, the processor processes the temperature data to determine if the temperature exceeds a time-dependent fever threshold, and the indicator generates a time-dependent indication of fever in an event the temperature data exceeds the time-dependent fever threshold.

The processor may process the temperature data of the individual to generate a time-corrected temperature data. The indicator may generate the time-dependent indication of fever by comparing the time-corrected temperature data of the individual against the time-dependent fever threshold. In some embodiments, the indicator may generate the time-dependent indication of fever by comparing the sensed temperature data of the individual against the time-dependent fever threshold.

Some embodiments relate to a temperature detector that includes a temperature sensor that obtains a temperature measurement and a processor that adjusts the temperature measurement according to a circadian cycle.

Certain embodiments relate to a method of processing temperature data that includes obtaining temperature data from large population and from the temperature data, determining a fever threshold, by employing a fever bump. The time-dependent fever indication may be a corrected individual temperature and/or a distribution of the temperature data.

Certain embodiments may include a circadian filter that adjusts the temperature measurement. The circadian filter may adjust the temperature measurement based on historical temperature data obtained over a circadian cycle from a group of individuals.

In some embodiments a reporter that reports the adjusted temperature measurement for use in detection of internal body conditions may be utilized. The reporter may report the adjusted temperature measurements of a plurality of individuals to a second processor that processes the adjusted temperature measurements to determine a body temperature data pattern for the plurality of individuals. The second processor may indicate a disease outbreak in a geographic area based on the body temperature data pattern.

In some embodiments, the reporter may report adjusted temperature measurements of a plurality of individuals to a second processor that processes the adjusted temperature measurements to indicate a disease outbreak in a geographic area based on a change in adjusted temperature measurements over a time period.

In certain embodiments, the processor may indicate presence or absence of fever in an individual based on the adjusted temperature measurement. Further, the processor may employ historical temperature data obtained over a circadian cycle from a group of individuals to obtain a threshold used for indication of fever. The processor may employ a local maximum (also referred to as a "fever bump" herein) of a plot of the historical temperature data to determine a threshold used for indication of fever. The processor may update the historical temperature data using the adjusted temperature. In some embodiments, the processor may employ a local maximum of a plot of historical temperature data obtained over a circadian cycle from a group of individuals to determine a threshold used for indication of fever. Further, the processor may adjust the temperature measurement based on statistical characteristics of the plot of historical temperature data. The statistical characteristics may include mean and standard deviation of the plot of historical temperature data.

In certain embodiments, the processor may employ historical temperature data obtained over a circadian cycle from an individual over time to obtain a threshold used for indication of fever. The processor may obtain the adjusted temperature measurement using the historical temperature data. In some embodiments, the processor may employ historical temperature data obtained over a circadian cycle from an individual over time to obtain a threshold used for indication of internal body conditions of an individual. Further, in some embodiments, the fever threshold may be adjusted by applying a circadian filter to the fever threshold. Stronger corrections may be applied to temperatures during low portions of the circadian cycle than to temperatures during the high portions of the temperature cycle.

Some embodiments may detect an individual temperature and, based on the fever threshold and the individual temperature, determine if the individual has a fever. In some embodiments, a circadian filter may be applied to an individual temperature. Certain embodiments may apply a circadian filter to the temperature data obtained from the large population.

Further, in some embodiments, the processor may adjust the temperature measurement according to a weighted mean of the circadian cycle. In certain embodiments, the processor may adjust the temperature measurement using an asymmetric correction of temperature relative to the circadian cycle.

In certain embodiments, the temperature detector may include/be coupled with an indicator that signals the presence of fever using at least one of an indicator light, sound, or alphanumerical text.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments of the invention follows.

Figure 1A:
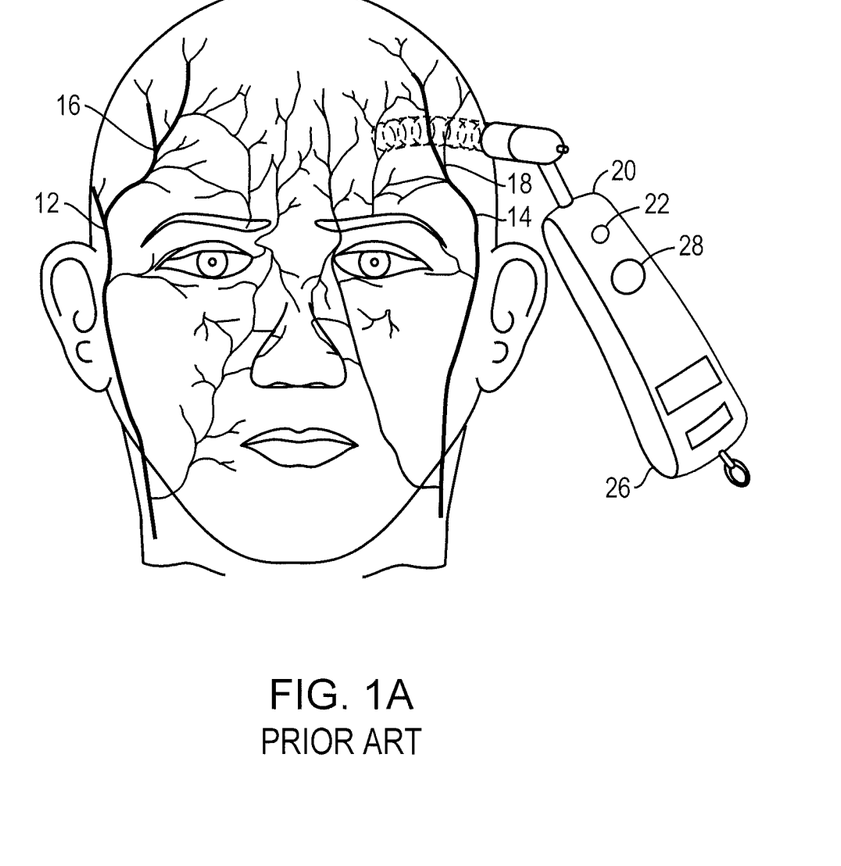
FIG. 1A is an example of a temporal artery thermometer that may be used with embodiments of the present invention.

FIG. 1A is an example of a temporal artery thermometer that may be used with embodiments of the present invention. Embodiments of the present invention are not limited to the use of infrared thermometers any other thermometer available in the art may be used with example embodiments of the invention. For example, certain embodiments may employ traditional mercury or resistance thermometers. Further, the temperature measurements may be obtained using available techniques in the art. For example, the temperature measurements may be oral, rectal, skin, ear, or temporal artery measurements.

The temporal artery (infrared) thermometer has been presented in U.S. Pat. No. 6,292,685, U.S. Pat. No. 7,346,386, and U.S. Pat. No. 7,787,938, the entire teachings of which are incorporated by reference herein. As shown in FIG. 1A, the forehead region of a human includes temporal arteries 12 and 14 that extend upwardly toward the side of the human face and bifurcate at 16 and 18 in the forehead region. In that region, the temporal artery passes over the skull bone very close to the skin and is thus termed the superficial temporal artery. The superficial temporal artery is, therefore, particularly accessible for providing temperature readings and, as an artery, has a temperature close to the heart temperature. Further, there are no known arterial/venus anastomoses, that is, shunts between the artery and veins for regulation of skin temperature. Accordingly, the blood flow is relatively stable, varying a maximum of only 50% as opposed to as much as 500% in other areas of the skin.

To locate the temporal artery, a temperature sensor, preferably a radiation detector 20, is scanned across the side of the forehead over the temporal artery while electronics in the detector search for the peak reading which indicates the temporal artery. Preferably, that temperature reading is then further processed in accordance with an algorithm specific to the temporal artery for providing a display temperature which may, for example, correspond to core, oral or rectal temperature.

Figure 1B:
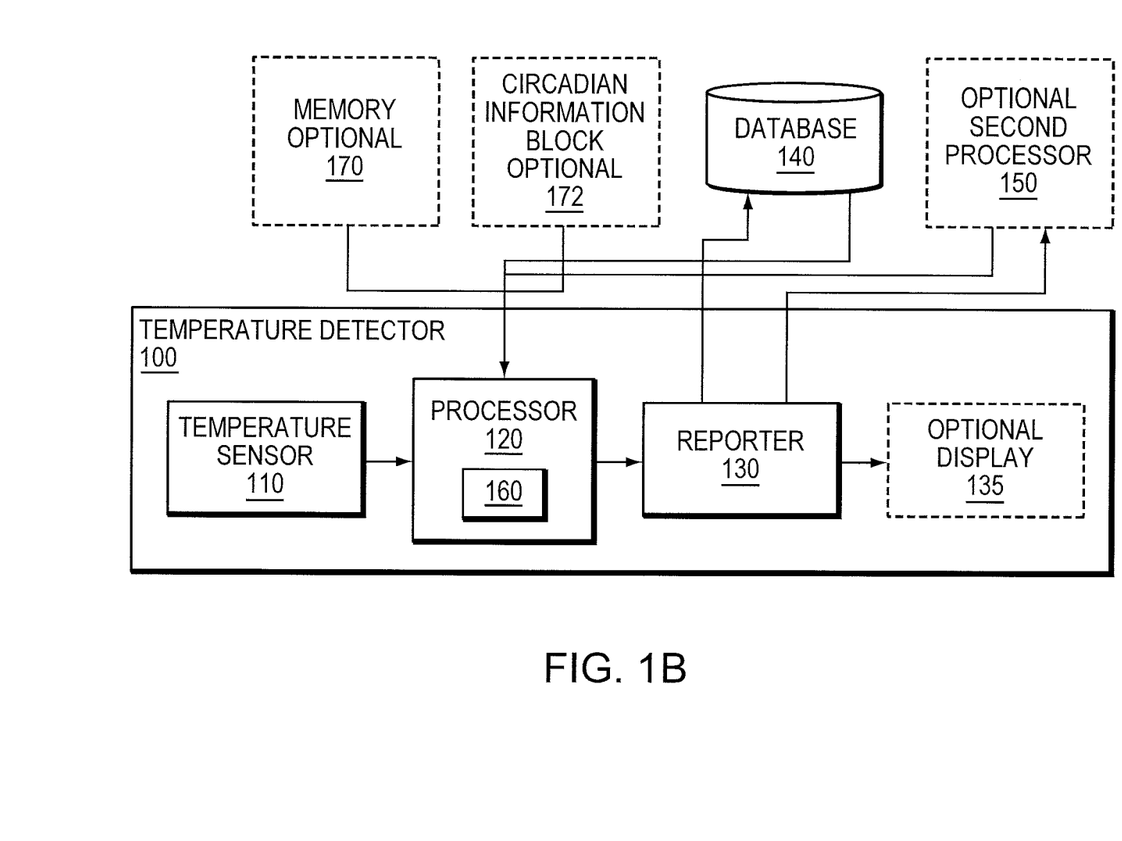
FIG. 1B is an example embodiment of a temperature detection system according to embodiments of the present invention.

FIG. 1B is an example embodiment of a temperature detection system 100 according to embodiments of the present invention. The temperature detection system 100 includes a temperature sensor 110 and a processor 120. The temperature sensor 110 obtains measurements of body temperature of one or more individuals. The temperature sensor 110 may be any of a rectal, oral, under arm, ear, or temporal artery thermometer. The processor 120 processes the temperature measurement obtained by the temperature sensor 110 and produces an adjusted temperature measurement that may be used in more accurate determination of body temperature and/or more accurate detection of fever.

In some embodiments, the processor 120 may be coupled with a reporter 130 that reports the adjusted temperature measurement. The adjusted temperature measurements may be reported to various outlets. For example, in some embodiments, the adjusted temperature measurements may be reported to a display 135 that displays the adjusted temperature. In some embodiments, the adjusted temperature measurement may be reported to an optional second processor 150 that performs further processing of the adjusted temperature measurements. In general, the adjusted temperature measurement may be reported to any unit/module that can use the data sample for evaluation and/or detection of internal body conditions (e.g., fever detection, cancer effects, tracking of thyroid function, and ovulation in females).

The reporter 130 may report the adjusted temperature measurement via any available communication technique in the art. For example, in certain embodiments, the reporter 130 may report the adjusted temperature data over a wireless communication link (as described in U.S. patent application Ser. No. 11/728,956, titled "Wireless Transmission of Temperature Data," the teachings of which are incorporated herein by reference).

In certain embodiments, the processor 120 may include a circadian filter 160 that adjusts the temperature measurements. The circadian filter 160 may employ historical temperature data from one or more individuals to adjust the temperature measurement. The historical temperature data may be obtained over a circadian cycle.

When using temperature measurements from a single individual, the temperature detector 100 may record temperature measurements obtained from the individual over time and employ the recorded temperature measurements to form a database 140 of historical temperature measurements. The temperature detector 100 may record the measurement directly into the database 140, into a memory unit 170, or any data storage/recording means known in the art.

The database 140 and/or the memory 170 may be internal or external to the temperature detector 100. If positioned externally, the temperature detector 100 may communicate with these units over any communication method known in the art, such as over a wireless communication link.

In order to determine the circadian information corresponding to the temperature measurements (e.g., time, date, season, etc.), the temperature detector 100 may utilize any available tool known in the art (labeled in FIG. 1, generally, as circadian information block 172). For example, the temperature detector may obtain the necessary information from an internal or external clock. In some embodiments, the temperature detector may connect to a remote server, base station, satellite, etc. to obtain the necessary circadian information. In some embodiments, an external processor may be utilized to receive and label (or time/date stamp) the temperature measurements with its corresponding circadian information.

Based on the historical data, a fever threshold may be determined. The fever threshold may be determined within the temperature detector 100, optionally by the processor 110 or by any other processor/computer unit included in the temperature detector (not shown). In certain embodiments, the fever threshold may be computed by a processor/computer (e.g., second processor 150) positioned external to the temperature detector 100 and forwarded to the temperature detector, optionally via a communication link.

When using temperature measurement from an individual to obtain historical temperature measurements, certain embodiments may require a predetermined minimum number of data samples (i.e., temperature measurements) before the circadian filter 160 can begin to adjust the temperature data based on historical temperature data.

In certain embodiments, the historical temperature data may be obtained from multiple individuals over a number of days over a long period of time. For example, in one embodiment temperature measurements obtained from patients entering one or more emergency rooms in a geographic area (e.g., patients entering emergency rooms in Longwood medical area, Boston, Mass.) may be used to form the historical temperature data. The temperature data may be obtained over a number of days (i.e., months, seasons, years, etc.). In some embodiments, the historical data may be time stamped to incorporate circadian information. For example, the historical data may be plotted to define a circadian cycle (i.e., 24-hour period).

The historical data may be used to obtain a threshold for more accurate determination of fever. As explained above, the historical temperature data may be stored within the temperature detector 100 or outside of the temperature detector 100, optionally in a database 140. The fever threshold may be obtained within the temperature detector 100 by the internal processor 120 or outside of the temperature detector 100 by another processor or computer (e.g., second processor 150). Further, the fever threshold may be stored into a memory 170 (or other storage medium) that may be internal or external to the temperature detector 100. If stored externally, the fever threshold may be communicated to the temperature detector 100 via a communication link.

In some embodiments, the processor may compare the measured body temperature (obtained from the temperature sensor) to the fever threshold and determine if body temperature of the individual being examined should be classified as a fever.

The temperature detector 100 may report the presence or absence of a fever using the reporter 130. In certain embodiments, the display 135 may be used to indicate if presence of a fever has been detected. In certain embodiments, the display 135 may display an adjusted number that indicates fever to the user (e.g., 104° F.). In some embodiments, alphanumerical characters may be used to indicate presence of a fever. Further, in certain embodiments, alarms in forms of light or sound indicators (e.g., flashing light, beeping sound) may be used to indicate presence of a fever.

In certain embodiments, the temperature detector 100 may utilize multiple temperature thresholds depending on the population from which the historical data has been taken. For example, a first set of historical temperature data may be obtained from adult patients visiting an emergency room over a predetermined period of time and a second set of data may be obtained from pediatric patients visiting a pediatric emergency room. In such embodiments, the temperature detector may be modified to adaptively adjust its fever threshold to the population of patients under study such that when working with adults the fever threshold obtained from the first dataset is used and when working with children the fever threshold obtained from the second dataset is used.

In certain embodiments, the fever threshold may be modified and/or updated based on newly acquired temperature data.

Further, in some embodiments, the adjusted temperature data may be reported to a module (e.g., second processor 150) that processes the adjusted temperature data, along with adjusted temperature data of other individuals in the same geographical area (e.g., school and airport), to determine a body temperature pattern. In certain embodiments, the processing of temperature data takes place within the temperature detector 100 (e.g., using internal processor 120). The body temperature pattern may be used in determining a disease outbreak (as described in U.S. patent application Ser. No. 11/787,651, titled "Wireless Transmission of Temperature Data for a Geographic Area," the teachings of which are incorporated herein by reference).

In some embodiments, the adjusted temperature data of a single individual may be processed to determine a temperature pattern for that person. This individual temperature pattern may be used in evaluating and/or indicating internal body characteristics. For example, the individual patterns may be used to indicate an underactive thyroid function or ovulation in a female individual.

Figure 2:
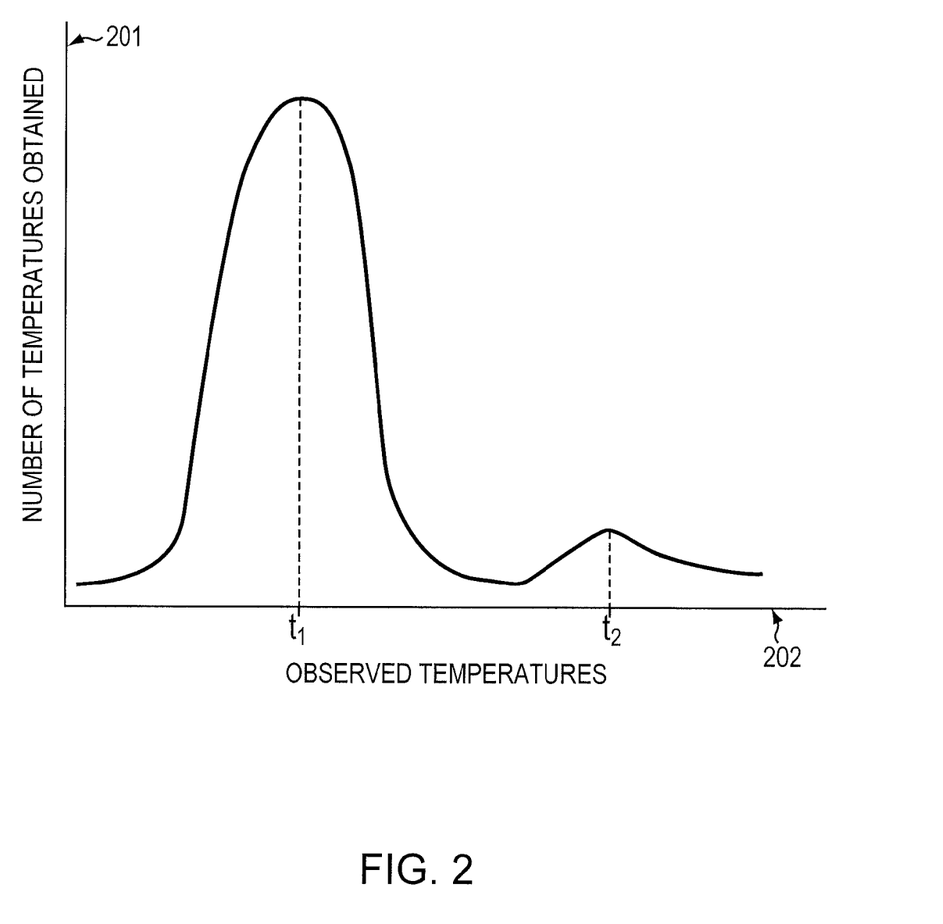
FIG. 2 illustrates an example of historical temperature data obtained from a plurality of individuals over time that may be used in obtaining a fever threshold.

FIG. 2 illustrates an example of historical temperature data obtained from a plurality of individuals over time that may be used in obtaining a fever threshold. As noted above, the historical data may be obtained from one or more individuals. If data points are obtained from a single individual, some embodiments may require that predetermined minimum number of data points be obtained before a fever threshold can be obtained. If obtained from multiple individuals, the temperature measurement data points may be obtained from various individuals, over a period of time, over one or more geographical locations.

For example, in one embodiment, data obtained from patients entering an emergency room in Boston may be used. In order to obtain the data, a temporal artery thermometer was used to take a single temperature measurement of each patient entering an emergency room in a Boston, Mass. area hospital.

Embodiments of the present invention are not limited to the use of infrared thermometers any other thermometer available in the art may be used with example embodiments of the invention. For example, certain embodiments may employ traditional mercury or resistance thermometers. As noted above, the temperature measurements may be obtained using available techniques in the art. For example, the temperature measurements may be oral, rectal, skin, ear, or temporal artery measurements.

The measurements were taken over time (over a number of days) at various hours and plotted over the range of observed temperatures. The plot shown in FIG. 2 illustrates an example of the graph obtained from plotting the temperatures over the range of observed temperatures. The values on the horizontal axis 201 generally illustrate the observe temperatures while the values on the vertical axis 202 illustrate the frequency of each temperature measurement observation.

Given the cost effectiveness, anonymity, and ease of use offered by the temporal artery thermometer, Applicants have been able to obtain over 70,000 temperature measurements. Once plotted, the observations result in a similar, although smoother, graph as that shown in FIG. 2.

As shown in FIG. 2, the plot of temperature observations demonstrates two maxima. The global maximum appears at temperature $T_1$, which in normal circumstances (e.g., no known pandemic of a disease) is at about 98° F. This indicates that the normal body temperature of majority of people visiting the emergency room under study is around the commonly known normal range of 98.6° F. Further, a second maximum, a local maximum, $T_2$, appears at higher temperatures at around 101° F., which again is in the vicinity of temperatures (100.4° F.-103° F.) commonly categorized as fever.

Certain embodiments of the present invention employ the plot shown in FIG. 2 to determine a threshold for indicating fevers. For example, certain embodiments may consider a temperature measurement falling above temperature $T_2$ as being an indication of a fever and classify temperatures falling below $T_2$ as being in the normal range.

In certain embodiments, statistical mean, 0, and standard deviation, G, of the plot may be obtained and used in calculating the fever threshold. Specifically, certain embodiments may declare any temperature measurement falling within $\mu+2\sigma$ of $T_1$ as being within the normal range. Similarly, certain embodiments may consider any temperature measurement falling within $\mu+2\sigma$ of $T_2$ as being indicative of a fever.

Figure 3:
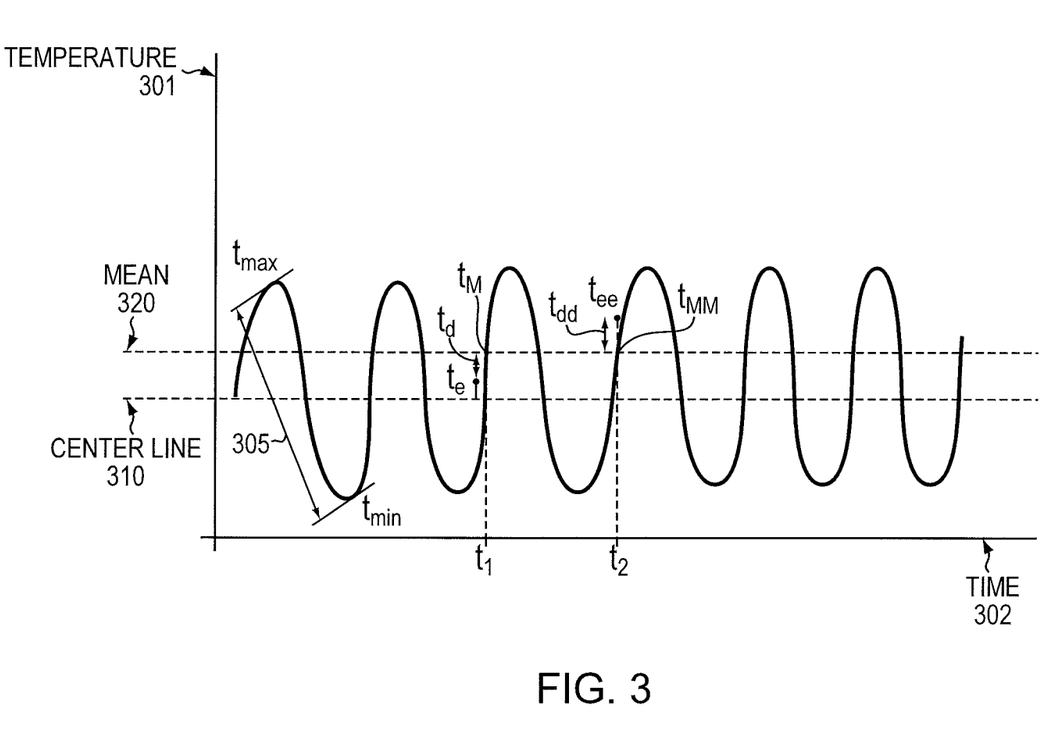
FIG. 3 is an example of circadian variations in human body temperature that may be used by embodiments of the present invention.

FIG. 3 is an example of circadian variations in human body temperature that may be used by embodiments of the present invention. The values shown on the horizontal axis 302 indicate time of the day and the values on the vertical axis denote temperature 301. As noted previously, human temperature may vary during a circadian cycle. For example, there may be a change of up to 1° F. in the temperatures observed over a circadian cycle. As shown in FIG. 3, the temperature may be at a minimum, $T_{min}$, at some point during the circadian cycle, for example at 6:00 AM. The temperature may reach a maximum, $T_{max}$, at some point during the circadian cycle, for example at 6:00 PM. Daily cycle is an important physiological feature of the humans. Accordingly, certain embodiments of the present invention may employ a circadian filter 160 (FIG. 1) that adjusts a temperature measurement while considering the circadian cycle to display a normalized temperature, corrected for time of day.

In certain embodiments, a weighted mean of the circadian cycle may be utilized to adjust the temperature data. Further, some embodiments may utilize an asymmetric correction for adjusting the temperature data over the circadian cycle. Specifically, since most of the temperature measurements obtained from individuals are typically obtained between the hours of 6:00 AM to 6:00 PM (range 305 shown on FIG. 3), the mean 320 of those measurements is weighted towards the temperature of waking hours and would be above the center temperature line 310 between the high and low peaks in the circadian cycle. As illustrated in FIG. 3, to compensate for this, the temperatures in the low portion of the circadian cycle are increased more than the temperatures in the high portion of the circadian cycle are decreased.

As shown, at time $t_1$, the expected temperature $T_e$ is below the mean $T_M$ by a difference amount $T_d$. Thus, at time $t_1$, within the cycle, as determined by historical data, the difference amount $T_d$ is added to an individual actual temperature. Thus, if a patient has normal temperature, the corrected temperature will be at the mean. However, in a patient who has a fever, the corrected temperature will be above the mean to indicate fever. This provides a time-dependent indication of fever.

Similarly, at time $t_2$, the expected temperature $T_{ee}$ is below the mean $T_{MM}$ by a difference amount $T_{dd}$. Thus, at time $t_2$, within the cycle, as determined by historical data, the difference amount $T_{dd}$ is subtracted from an individual actual temperature. The corrected temperature is then compared to a predetermined fever threshold to determine whether a fever exists and, if so, the fever indication may be activated.

The fever threshold may be established through conventional calculation of $\mu+2\sigma$. Preferably, the threshold is determined by the fever bump of the distribution.

As an alternative to correcting the sensed temperature, the fever threshold may vary with the circadian cycle. To that end, an individual temperature distribution may be determined for each temperature window.

Circadian filtering may be applied to the population data to obtain a distribution as shown in FIG. 2, for each time window (hourly). Each distribution may allow for detection of fever threshold for that time window. Fever threshold may be determined using the $\mu+2\sigma$ approach or the fever bump approach.

In some embodiments, further processing, manipulation, and/or interpolation of temperature data may be done prior to determining the fever threshold.

In some embodiments, the thermometer may tailor itself to an individual. This may be done using a TAT (Temporal Artery Thermometer) per patient setting. In certain embodiments, a single thermometer may be arranged for obtaining adjusted temperature data from multiple patients.

Further, certain embodiments may employ historical temperature data in determining accurate body temperature. The prior data, if taken at sufficiently small intervals, shows a circadian cycle pattern. However, data taken at other intervals may show patterns over a longer time frame (e.g., seasonal). The minimum resolution of the data would be dependent on the purpose.

Certain embodiments may employ patterns other than (or in addition to) the circadian cycle. For example, in certain embodiments, temperature measurements may be adjusted depending on time of year, location, age of patient, etc. In some embodiments may perform further processing and analysis of temperature data based on other patterns and temperature or non-temperature related information.

The adjusted temperature obtained from embodiments of the present invention may optionally be used in monitoring or detection of optimal alertness or performance. Greater alertness and higher performance are correlated with higher temperature. This correlation may be applied to non-subjective determination of alertness on jobs or missions that require a certain high degree of alertness (e.g., fighter pilots, high speed train conductors, astronauts, etc).

Certain embodiments may obtain data on different population sets (e.g., age group, sex, and ambulatory vs. non-ambulatory), derive temperature profiles for the population sets (with corresponding statistical error bars), and use the relevant profile for comparison to a patient to determine if he or she is in the normal range.

Further, some example embodiment may provide for charting capability. Specifically, example embodiments may be used to obtain an extended data set for either one person or many persons allows any periodicity to be seen or detected. Such embodiments may be used to detect diseases that have fever periodicity (e.g., every 24 hours (malaria), every 48 hours (tertian fever type of malaria), every 72 hours (quartan fever type of malaria), weekly (typhoid fever), etc). This may be applicable in a one-thermometer-per-patient situation. If such patterns are detected, an alert may be sent to a doctor.

Areas that cannot afford even simple laboratory diagnostic tests often use only a history of subjective fever as the indication to treat for malaria. Using Giemsa-stained blood smears from children in Malawi, one study showed that when clinical predictors (rectal temperature, nailbed pallor, and splenomegaly) were used as treatment indications, rather than using only a history of subjective fevers, a correct diagnosis increased from 21% to 41% of cases, and unnecessary treatment for malaria was significantly decreased. The use of a Sentinel-type system, according to embodiments of the present invention, may enhance detection of malaria, and temporal artery temperature would probably be a welcome substitute for rectal temperature.

Certain embodiments may be used in Basal body temperature (BBT) charting to determine when and if ovulation has occurred. Charting the temperature daily over one or more months allows the biphasic temperature pattern to be seen. A woman's temperature will increase by a small amount once ovulation has occurred. Accordingly, certain example embodiments may be used in detecting temperature of a human subject and providing a chart (e.g., shown above) that may be used in family planning.

Certain embodiments of the invention employ rapid communication that allows medical steps to be taken sooner, allows temperatures to be monitored closer to real-time (as opposed to infrequent office visits, for example). In some cases, it may be necessary to identify the patient, with either a name or a number. In other cases, identifying the patient is not necessary or is forbidden due to privacy laws. In yet other cases, there may only be one user of the thermometer and information related specifically to the user would be contained in the equipment. The information may be sent to doctor, a call center, a person in charge, a local or remote piece of equipment, or a handheld device (e.g., an iPhone). The information may be used for decision-making, and/or result in an action like an alert, or could be used for creating a data history for some future use. Communication may be two-way, since cell phone modules allow receipt of messages as well as transmission. It may be possible for example embodiments to alter the firmware or firmware parameters in the temperature detection unit remotely. Options include regular updates, periodic checks to see if updates are necessary, and the "pulling" of information by the unit. Some examples where rapid communication would be advantageous include:

Heat exhaustion/heat stroke/hyperthermia in athletes (e.g., in sports practices) at various points at a marathon, etc. Athletes (especially football players, due to their equipment and uniform) have died during practice due to heat exhaustion and heat stroke. Periodic checks would allow them to be monitored for the raised temperatures associated with heat exhaustion. Marathon runners could be checked along the marathon route, not just at the end of the route.

Fever monitoring in neutropenia/chemotherapy patients. A message could be automatically sent to a doctor if the temperature is above a certain threshold. Neutropenia and chemotherapy patients have a compromised immune system, so any infection is serious. An elevated temperature associated with infection could be detected quickly and conveniently, and lead to treatment sooner.

Monitoring of foot temperatures of diabetic neuropathy patients—periodic reports or messages lets doctors know that patients are not neglecting foot care. The feet of a diabetic can suffer from nerve damage. This means that vigilant monitoring of the condition of the feet is necessary to prevent problems that are only treatable by amputation. The Sentinel system according to example embodiments adds the feature of communication of temperatures to a healthcare worker.

Real-time monitoring by health officials, plant managers, airport screeners, etc. Identification would not be necessary, and in the case where the public is involved, identification may be proscribed. The historical data obtained from multiple individuals may be used to track where a flu pandemic starts, where and how it spreads. Accordingly, the embodiments are able to detect a pandemic much faster than conventional methods, and alert health officials when there is a possible pandemic.

Certain example embodiment may provide for more convenient data-logging. For example, using example embodiments, during sleep studies that take the temperature of patients, it is not necessary to wake or disturb the patient. It is also more convenient physically because there are no wires or cables. It is also more convenient logistically because the data does not need to be written down and typed into a computer.

Certain example embodiment may provide for private data logging. The data may also be sent to a user selectable telephone number or email address. Such data logging may be done by an individual or by an institution, such as a research institute, large companies, etc.

Certain example embodiment may include a reminder system. The thermometer may emit a sound or display a message as a reminder to take a temperature. The reminder may either be sent from a call center, or programmed into the thermometer.

Certain example embodiment may include non-temperature data. Data other than temperature may be sent back to a call center or a processor center. For example, ambient data temperatures may be sent back to a processing center so that the ambient conditions in which the thermometer is used can be determined.

Certain example embodiment may employ the obtained temperature data for non-patient related purposes. The temperature data may be analyzed to determine when an instrument requires cleaning Dirty lenses result in decreased readings in general. A message may then be sent to the owner of the thermometer or to the thermometer itself, to clean the instrument.

The temperature detector may be equipped with memory. There may be a memory recall feature for the user's own knowledge. The memory may be used to store batches of data if sending batches of data was preferred, due to the increased cost of sending each temperature as a single message.

The temperature detector may be equipped with a switch that allows the user to select either a) send every temperature as it is taken, or b) send a batch of temperatures.

The temperature detector may include a holder capable with IR communication. The thermometer itself may be capable of IR communication. The holder may be hooked up to a computer (necessary just once) to set the destination cell phone number or email address in the thermometer. The holder may optionally have a graphical display and display the data.

The temperature detector may include a recharging circuitry and be able to use rechargeable batteries.

While this invention has been particularly shown and described with references to example embodiments thereof, it will be understood by those skilled in the art that various changes in form and details may be made therein without departing from the scope of the invention encompassed by the appended claims.

What is claimed is:

1. A temperature detector comprising:
   a temperature sensor that obtains a temperature measurement of an individual; and
   a processor that includes a circadian filter that adjusts the temperature measurement to generate a time-corrected temperature measurement to establish more accurate detection of fever.

2. The temperature detector of claim 1 further comprising a display of the time-corrected temperature measurement.

3. The temperature detector of claim 1 wherein the circadian filter adjusts the temperature measurement based on historical temperature data obtained over a circadian cycle from a group of individuals.

4. The temperature detector of claim 1 further including a reporter that reports the time-corrected temperature measurement for use in detection of internal body conditions.

5. The temperature detector of claim 4 wherein the reporter reports time-corrected temperature measurements of a plurality of individuals to a second processor that processes the time-corrected temperature measurements to determine a body temperature data pattern for the plurality of individuals.

6. The temperature detector of claim 5 wherein the second processor indicates a disease outbreak in a geographic area based on the body temperature data pattern.

7. The temperature detector of claim 4 wherein the reporter reports time-corrected measurements of a plurality of individuals to a second processor that processes the time-corrected temperature measurements to indicate a disease outbreak in a geographic area based on a change in time-corrected temperature measurements over a time period.

8. The temperature detector of claim 1 wherein the processor indicates presence or absence of fever in an individual based on the time-corrected temperature measurement.

9. The temperature detector of claim 1 wherein the processor employs historical temperature data obtained over a circadian cycle from a group of individuals to obtain a threshold used for indication of fever.

10. The temperature detector of claim 9 wherein the processor employs a local maximum of a plot of the historical temperature data to determine a threshold used for indication of fever.

11. The temperature detector of claim 9 wherein the processor updates the historical temperature data using the time-corrected temperature measurement.

12. The temperature detector of claim 1 wherein the processor employs a local maximum of a plot of historical temperature data obtained over a circadian cycle from a group of individuals to determine a threshold used for indication of fever.

13. The temperature detector of claim 12 wherein the processor adjusts the temperature measurement based on statistical characteristics of the plot of historical temperature data.

14. The temperature detector of claim 13 wherein the statistical characteristics include mean and standard deviation of the plot of historical temperature data.

15. The temperature detector of claim 1 wherein the processor employs historical temperature data obtained over a circadian cycle from an individual over time to obtain a threshold used for indication of fever.

16. The temperature detector of claim 15 wherein the processor obtains the time-corrected temperature measurement using the historical temperature data.

17. The temperature detector of claim 1 wherein the processor employs historical temperature data obtained over a circadian cycle from an individual over time to obtain a threshold used for indication of internal body conditions of an individual.

18. A method for detecting temperature comprising:
    obtaining a temperature measurement of an individual using a temperature sensor; and
    processing the temperature measurement using a circadian filter that adjusts the temperature measurement to generate a time-corrected temperature measurement to establish more accurate detection of fever.

19. The method of claim 18 further including adjusting the temperature measurement based on historical temperature data obtained over a circadian cycle from a group of individuals.

20. The method of claim 18 further including reporting the time-corrected temperature measurement for use in detection of internal body conditions.

21. The method of claim 20 further including processing the reported time-corrected temperature measurement to determine a body temperature data pattern for the plurality of individuals.

22. The method of claim 21 further including indicating a disease outbreak in a geographic area based on the body temperature data pattern.

23. The method of claim 21 further including processing the time-corrected temperature measurements to indicate a disease outbreak in a geographic area based on a change in time-corrected temperature measurements over a time period.

24. The method of claim 18 further including indicating presence or absence of fever in an individual based on the time-corrected temperature measurement.

25. The method of claim 18 further including determining a threshold used for indication of fever using historical temperature data obtained over a circadian cycle from a group of individuals.

26. The method of claim 25 further including determining a threshold used for indication of fever using a local maximum of a plot of the historical temperature data.

27. The method of claim 25 further including updating the historical temperature data using the time-corrected temperature measurement.

28. The method of claim 18 further including determining a threshold used for indication of fever using a local maximum of a plot of historical temperature data obtained over a circadian cycle from a group of individuals to determine a threshold used for indication of fever.

29. The method of claim 28 further including adjusting the temperature measurement based on statistical characteristics of the plot of historical temperature data.

30. The method of claim 29 wherein the statistical characteristics include mean and standard deviation of the plot of historical temperature data.

31. The method of claim 18 further including determining a threshold used for indication of fever using historical temperature data obtained over a circadian cycle from an individual over time.

32. The method of claim 31 further including determining the time-corrected temperature measurement using the historical temperature data.

33. The method of claim 18 further including determining a threshold used for indication of internal body conditions of an individual using historical temperature data obtained over a circadian cycle from an individual over time.

34. A method of processing temperature data comprising:
obtaining temperature data from large population; and
from the temperature data, determining a fever threshold by employing a fever bump.

35. The method of claim 34 further comprising detecting an individual temperature and, based on the fever threshold and the individual temperature, determining if the individual has a fever.

36. The method of claim 35 further comprising applying a circadian filter to an individual temperature.

37. The method of claim 34 further comprising applying a circadian filter to the temperature data obtained from the large population to define individual temperature distributions for different times and determining a fever threshold for each time.

38. A temperature detector comprising:
a temperature sensor that obtains temperature data from a large population; and
a processor that processes the temperature data to determine a fever threshold from a fever bump.

39. The temperature detector of claim 38 wherein the processor indicates if an individual has a fever based on the fever threshold and the individual temperature.

40. The temperature detector of claim 38 wherein the processor includes a circadian filter that adjusts the temperature data obtained from the individual.

41. The temperature detector of claim 38 wherein the processor includes a circadian filter that adjusts the temperature data obtained from the large population.

42. The temperature detector of claim 38 further including an indicator that signals presence of fever in an event temperature of an individual exceeds the fever threshold determined by the processor.

43. The temperature detector of claim 42 wherein the indicator signals the presence of fever using at least one of an indicator light, sound, or alphanumerical text.

44. The temperature detector of claim 1 wherein the processor adjusts the temperature measurement according to a weighted mean of the circadian cycle.

45. The temperature detector of claim 1 wherein the processor adjusts the temperature measurement using an asymmetric correction of the circadian cycle.

46. A temperature detector comprising:
a temperature sensor that obtains temperature data from a plurality of individuals;
a processor that processes the temperature data to generate time-corrected temperature data and to determine if the temperature exceeds a time-dependent fever threshold; and
an indicator that generates a time-dependent indication of fever in an event the temperature data exceeds the time-dependent fever threshold.

47. The temperature detector of claim 46 wherein the indicator generates the time-dependent indication of fever by comparing the time-corrected temperature data of the individual against the time-dependent fever threshold.

48. The temperature detector of claim 46 wherein the indicator generates the time-dependent indication of fever by comparing the sensed temperature data of the individual against the time-dependent fever threshold.

* * * * *